United States Patent
Sota et al.

(10) Patent No.: US 6,350,426 B1
(45) Date of Patent: Feb. 26, 2002

(54) METHOD OF DETERMINING COMPONENT CONCENTRATIONS IN THREE-COMPONENT MIXTURE AND METHOD OF CONTINUOUS PRODUCTION OF HYDROGEN FLUORIDE USING THE METHOD

(75) Inventors: Tomizo Sota; Toshinobu Takeuchi; Ichiro Morioka, all of Settu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/155,096

(22) PCT Filed: Mar. 19, 1997

(86) PCT No.: PCT/JP97/00894

§ 371 Date: Feb. 8, 1999

§ 102(e) Date: Feb. 8, 1999

(87) PCT Pub. No.: WO97/35187

PCT Pub. Date: Sep. 25, 1997

(30) Foreign Application Priority Data

Mar. 19, 1996 (JP) ............................................. 8-090228

(51) Int. Cl.[7] ............................ C01B 7/19; G01N 29/18; G01N 27/06; G01N 11/00
(52) U.S. Cl. ...................... 423/485; 423/483; 73/61.43; 73/61.46; 73/61.49
(58) Field of Search ............................... 73/61.43, 61.46, 73/61.49; 423/483, 485, 522, 531

(56) References Cited

U.S. PATENT DOCUMENTS

| | | | | |
|---|---|---|---|---|
| 2,430,963 A | * | 11/1947 | Stephenson et al. | 423/467 |
| 3,878,294 A | * | 4/1975 | Schabacher et al. | 423/485 |
| 4,520,654 A | * | 6/1985 | Terhune | 73/24 |
| 5,271,918 A | * | 12/1993 | Patterson et al. | 423/485 |
| 5,518,933 A | * | 5/1996 | Ishibashi | 73/61.46 |
| 5,851,837 A | * | 12/1998 | Stokes et al. | 436/149 |

FOREIGN PATENT DOCUMENTS

| | | | |
|---|---|---|---|
| JP | 49-037898 | * | 4/1974 |
| JP | 5-026853 | * | 2/1993 |

* cited by examiner

Primary Examiner—Ngoc-Yen Nguyen
(74) Attorney, Agent, or Firm—Connolly Bove Lodge & Hutz (57) ABSTRACT

A method of quickly and safely determining the component concentrations of a three-component mixture comprising substantially sulfuric acid, hydrogen fluoride and water, which comprises measuring at least one set of three physical quantities of (1) temperature, (2) ultrasonic wave propagation velocity and (3) electric conductivity or viscosity of the three-component mixture and converting the obtained values to the component concentrations on the basis of a working curve representing the relationship between each component concentration of the three-component mixture and the three physical quantities; and a method of continuous production of hydrogen fluoride for controlling a water concentration in the reaction system by using this method.

8 Claims, 5 Drawing Sheets

METHOD OF DETERMINING COMPONENT CONCENTRATIONS IN THREE-COMPONENT MIXTURE AND METHOD OF CONTINUOUS PRODUCTION OF HYDROGEN FLUORIDE USING THE METHOD

FIELD OF THE INVENTION

The present invention relates to a method of determining the concentrations of components of a ternary mixture essentially consisting of sulfuric acid, hydrogen fluoride, and water and to a process for continuous production of hydrogen fluoride which comprises using the method.

PRIOR ART

Any method for determining the concentration of a given component of a mixture comprising a plurality of chemical substances of known kinds indirectly and expediently with a method other than direct determinations is expected to find application in many fields. For binary mixtures, several practical methods are known but when it comes to a ternary mixture, no effective method has been available.

Therefore, in determining the concentration of water in a ternary mixture containing water, for instance, it is common practice to sample the ternary mixture and quantitate the water therein with a direct method such as Karl Fischer's method.

However, the direct method for quantitating a component of a ternary mixture is not only generally time-consuming and unsuited for applications requiring rapid determinations but often involves fairly large errors.

Furthermore, when such a ternary mixture contains a substance harmful to human beings, the direct determination and the necessary sampling have the disadvantage of involving risks for health hazards.

Meanwhile, hydrogen fluoride is a starting material of great importance for the production of various fluororesins and fluorine-containing compounds. Commercially, hydrogen fluoride can be obtained by reacting fluorspar with sulfuric acid. In the commercial production of hydrogen fluoride with this reaction, a high-boiling mixture containing unreacted sulfuric acid is not treated off-line but recycled for reuse.

The process in common use today comprises the following steps.

Thus, the process is a continuous production process comprising (1) a step of reacting the material fluorspar with starting sulfuric acid, (2) a step of separating the crude reaction product obtained in step (1) into (a) a low-boiling mixture composed predominantly of hydrogen fluoride and (b) a high-boiling mixture composed predominantly of unreacted sulfuric acid and containing small proportions of hydrogen fluoride and water, (3) a step of purifying and isolating hydrogen fluoride from said low-boiling mixture (a), a step (4) of adding a substantially equivalent amount of sulfuric anhydride to said high-boiling mixture (b) to form sulfuric acid through reaction with water to thereby convert substantially all the water to sulfuric acid and returning it together with unreacted sulfuric acid as sulfuric acid feed back to said step (1), and a step (5) of adding sulfuric acid in a supplemental amount to make the necessary amount of sulfuric acid available for reaction with the fluorspar.

The above steps are now described in further detail.

In the above step (1), which includes a kneading and heating stage, the starting fluorspar and sulfuric acid are introduced into a reaction system comprising a kneader and a kiln through respective the ducts and mechanically kneaded and reacted in the kiln under heating at 400 to 500° C. This reaction between fluorspar ($CaF_2$) and sulfuric acid ($H_2SO_4$) proceeds as follows to give hydrogen fluoride.

Concurrently, the trace impurities in the material fluorspar, i.e. silicon oxide and calcium carbonate, give rise to water and other byproducts as follows.

In order to provide hydrogen fluoride of high purity, a step of removing the unreacted feed and those byproducts is required.

Therefore, in the above step (2), the reaction product crude gas from said mixing and heating stage is fed to a crude gas washing column for washing and primary purification. This crude gas washing column has somewhat dissimilar functions between its upper zone and lower zone. Thus, the high-temperature crude gas generated from the reactor is first introduced into the bottom of the crude gas washing column and a high-boiling mixture (b) composed predominantly of sulfuric acid and accumulated in a reservoir tank disposed below said crude gas washing column is pumped up into the lower zone of the column at a level slightly below its middle portion to cause it to contact the ascending high-temperature crude gas to thereby remove the dust entrained from the reaction stage. Meanwhile, in the upper zone of the column, the liquid hydrogen fluoride available on condensation in a downstream stage and introduced from the column top is caused to contact the ascending dust-free crude gas to thereby remove a high-boiling fraction (sulfuric acid and water) through a condensation effect, while the low-boiling mixture (a) composed predominantly of hydrogen fluoride is withdrawn from the top of said crude gas washing column.

Then, in step (3), the low-boiling mixture (a) withdrawn in the above washing stage is purified to give the objective hydrogen fluoride of high purity.

The sulfuric acid occurring in the high-boiling mixture (b) separated in the above washing stage can be reused in the hydrogen fluoride-forming reaction for effective utilization of resources and should not be discarded for avoiding environmental pollution. Therefore, a step for recycling it as starting sulfuric acid is required.

Therefore, in the above step (4), provided is a stage in which the high-boiling mixture (b) separated in the above-mentioned washing stage is introduced into a mixing tank, while sulfuric anhydride (usually in the form of fuming sulfuric acid) is added to the tank so as to cause it to react with the byproduct water to give sulfuric acid, and fresh sulfuric acid is supplementarily added in an amount sufficient to make a substantially total necessary amount of starting sulfuric acid available for reaction with the material fluorspar for feeding to said kneading and heating stage.

In the stage described just above, when the amount of water is too large in comparison with sulfuric anhydride, the water in the sulfuric acid feed retards the reaction and the reaction product tend to form deposits and cakes. At the same time, corrosion of the equipment and pipeline proceeds throughout the whole recycling process. Therefore, in order that the amount of water will not be excessive, the amount of sulfuric anhydride to be added to the mixing tank must be accurately determined according to the amount of water occurring in the high-boiling mixture (b). As an important factor, the concentration of water in said high-boiling mixture (b) must be accurately determined in the above step (4).

Heretofore, this determination of water content has been carried out directly by sampling the high-boiling mixture from the duct constructing the production system at timed intervals and determining the concentration of water by Karl-Fischer's or other method.

However, such method has the disadvantage that the sampling procedure itself involves handling of hydrogen fluoride and sulfuric acid, both of which are dangerous substances. Moreover, there is a fair time lag before acquisition of data following said sampling and this failure to generate real-time information results in being late in accurately controlling the amount of supply of sulfuric anhydride.

SUMMARY OF THE INVENTION

Developed in the above state of the art, the present invention has for its object to provide a method of determining the concentration of any given component of a ternary mixture which is rapid, involving minimal errors, and safe procedure-wise and to provide a process for continuous production of hydrogen fluoride which comprises using the method.

The method of the invention, designed to accomplish the above object, is a method of determining the concentration of each component of a ternary mixture essentially consisting of sulfuric acid, hydrogen fluoride, and water, which comprises measuring at least one set of the three physical quantities, namely (1) temperature, (2) ultrasound propagation velocity, and (3) electrical conductivity or viscosity, of the ternary mixture and converting measured values to the concentrations of the respective components according to calibration curves representing the relationships of the concentrations of respective components of a ternary mixture composed of sulfuric acid, hydrogen fluoride, and water with the above-mentioned three physical quantities as separately constructed beforehand.

The concentration determination according to the invention can be carried out typically in the following manner. Thus, for example, while the ternary mixture to be analyzed for the concentration of any component thereof is maintained at a given temperature, its ultrasound propagation velocity and either electrical conductivity or viscosity are measured and the measured values are converted to the concentration of the corresponding component with reference to the above-mentioned calibration curves.

The process of the invention for continuous production of hydrogen fluoride comprises (1) a step of reacting starting fluorspar with starting sulfuric acid, (2) a step of separating a crude reaction product as obtained in step (1) into (a) a low-boiling mixture composed predominantly of hydrogen fluoride and (b) a high-boiling mixture composed predominantly of unreacted sulfuric acid and containing small proportions of hydrogen fluoride and water, (3) a step of purifying and isolating hydrogen fluoride from said low-boiling mixture (a), (4) a step of adding sulfuric anhydride to said high-boiling mixture (b) in a substantially equivalent amount with respect to the water to convert substantially all the water to sulfuric acid and returning it together with said unreacted sulfuric acid as sulfuric acid feed to said step (1), and (5) a step of adding sulfuric acid in a supplemental amount to provide the amount of sulfuric acid needed for reaction with starting fluorspar, wherein, in said step (4), the amount of water occurring in said high-boiling mixture (b) is determined by the method of the invention for determining the component concentration, particularly the concentration of water, of a ternary mixture.

Figure 5:
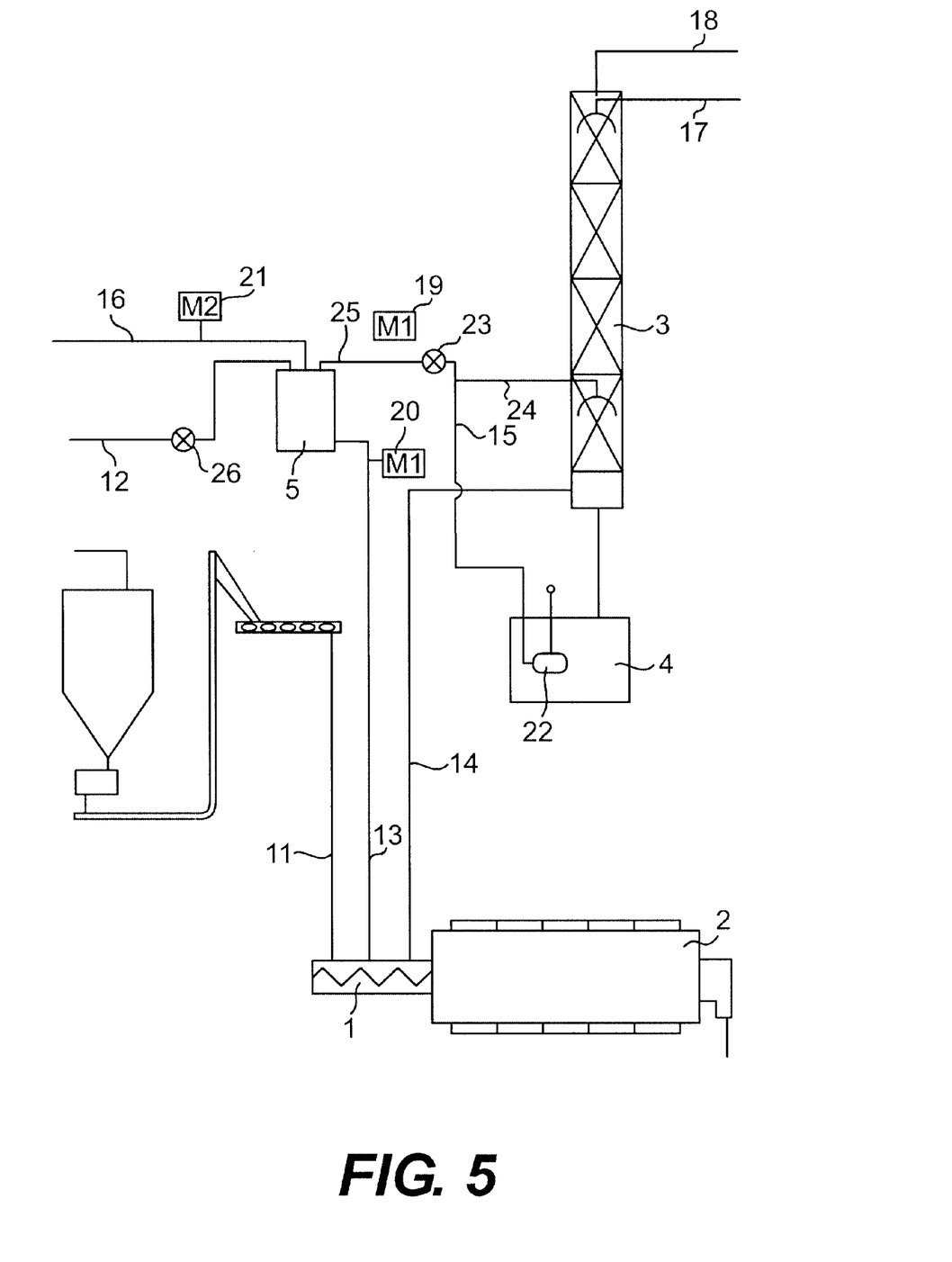
FIG. 5 is a schematic diagram showing a typical equipment as used in practicing the process of the invention for continuous production of hydrogen fluoride in Example 2.

The legends represent the following elements.
1 Kneader
2 Kiln
3 Crude gas washing column
4 Reservoir tank
5 Mixing tank
19 Means for measuring ultrasound propagation velocity and electrical conductivity
20 Means for measuring ultrasound propagation velocity and viscosity
21 Means for sulfuric anhydride supply means
23, 26 Flow control valves

DETAILED DESCRIPTION OF THE INVENTION

The present invention is now described in detail.

The method of determining the concentrations of components of a ternary mixture according to the invention (component concentration determination method) is explained in the first place.

The mixture to which the component concentration determination method of the invention can be applied with advantage is a ternary mixture essentially consisting of sulfuric acid, hydrogen fluoride, and water. The term "essentially" is used herein to mean that although other trace components may be contained, the components to be determined are only the three of sulfuric acid, hydrogen fluoride, and water.

The concentrations of three components of said ternary mixture are not particularly restricted but the usual mixture to be analyzed is a mixture comprising 70 to 100 weight % of sulfuric acid, 0 to 30 weight % of hydrogen fluoride, and 0 to 30 weight % of water. In the process of the invention for continuous production of hydrogen fluoride, which is described in detail hereinafter, the concentrations of components of the ternary mixture involved are within the above-mentioned ranges.

In the component concentration determination method of the invention, the three physical quantities of (1) temperature, (2) ultrasound propagation velocity, and (3) either electrical conductivity or viscosity in each set are measured for a ternary mixture of known component concentrations in the first place. These measurements are carried out for constructing the calibration curves of the invention which represent the correlation between the concentration of each of said three components with said three physical quantities.

The component concentration determination method of the invention was established by the inventors of the present invention as the result of their discovery, for the first time, of the existence of a reproducible correlation between the concentration of each component of a ternary mixture and said three physical quantities.

Ultrasonic determination of the concentration of each component of a binary mixture is a known technology. Thus, generally the ultrasound propagation velocity in a solution varies with the concentration of the component and the temperature of the solution. Therefore, by measuring the ultrasound propagation velocity of a solution at a given temperature, the concentration of the component can be determined.

On the other hand, an analysis by the inventors revealed that in a ternary mixture such as the high-boiling mixture (b) available in the above-mentioned process for continuous production of hydrogen fluoride, mere determination of ultrasound propagation velocity at a given temperature resulted in a considerable error in the concentration found and that the concentration of each component in a ternary mixture cannot be accurately determined by the conventional ultrasound propagation velocity technique.

In accordance with the present invention, the concentration of water in a ternary system can be determined with high accuracy as described in detail below.

Construction of the above-mentioned calibration curves is first described.

Basically, sets of two physical quantities other than temperature are first measured at every temperature for liquid ternary mixtures of every component concentration at atmospheric pressure (Usually, ternary mixtures of component concentrations varying at 1 or 2 weight % intervals are analyzed at temperatures varying at 5° C. intervals and the respective physical quantities at the inbetween concentrations and temperatures are respectively determined by proportional approximation from the two nearest measured values on both sides) and the two kinds of measured physical quantities are plotted on the vertical and horizontal axes, respectively, to construct calibration curves.

The following explanation is made with reference to concentration but the same applies to temperature as well.

To construct calibration curves, ternary mixtures of known component concentrations are first prepared. Such ternary mixtures can be prepared by, for example, the following procedure.

First, mixtures of water and hydrogen fluoride, among the components of the objective ternary mixture, are prepared in various concentration ratios. Then, predetermined amounts of sulfuric acid are added to aliquots of the above mixtures to provide a predetermined number of ternary mixtures of varying component concentrations.

Thus, generally a total of 961 different ternary mixtures of sulfuric acid, hydrogen fluoride, and water varying in the concentration of hydrogen fluoride at 1 weight % intervals between 0 and 30 weight % and the concentration of water varying at 1 weight % intervals between 0 and 30 weight % can be provided. For explanation's sake, those mixtures are referred to hereinafter as Lot 1, Lot 2, . . . , Lot 961.

To construct exact calibration curves, the above 961 different ternary mixtures are prepared in triplicate and the three physical quantities are measured for each lot and the mean values are calculated.

The ternary mixtures prepared in the above manner are held at a predetermined temperature. Such temperature setting can be carried out by the usual method. For example, immersing a vessel or cell containing the mixture in a thermostat may be mentioned. As the above-mentioned temperature, it is preferable to use temperature which does not affect the concentrations of said three components under atmospheric pressure, namely within the range in which they remain liquid, for example 15° C. and 45° C.

The material of the vessel or cell must be resistant to the ternary mixture.

After the above temperature setting, ultrasound propagation velocity is measured for said ternary mixtures while they are held at a constant temperature. The instrument for measuring ultrasound propagation velocity is not particularly restricted only if it is capable of measuring ultrasound propagation velocity. For example, an instrument based on the sing around method is preferred.

The measured ultrasound propagation velocity values are recorded for Lot 1, Lot 2, . . . , Lot 961, respectively.

Then, with the temperature kept constant as above, electrical conductivity is measured for the ternary mixtures. The instrument for measuring electrical conductivity may, for example, be of such a construction that a magnetic field is applied in a direction perpendicular to a vessel holding an electrically conductive liquid, a couple of electrodes are disposed opposite each other in a direction perpendicular to the direction of the magnetic field, and the voltage generated by electromagnetic induction between the electrodes is measured to determine electrical conductivity.

The measured electrical conductivity values are recorded for Lot 1, Lot 2, . . . , and Lot 961, respectively.

Based on the two physical quantities thus determined by plotting, for instance, the ultrasound propagation velocity values on the horizontal axis and the electrical conductivity values on the vertical axis, respectively, a set of 961 plots, namely Lot 1, Lot 2, . . . , and Lot 961, is obtained on a graph.

The determination of viscosity is carried out using a viscometer with the temperature being held constant as above. The measured viscosity values are recorded for the respective lots as above. The viscometer may be virtually any type of one capable of measuring viscosity of liquid.

The two physical quantities, viz. ultrasound propagation velocity and viscosity, are plotted in the same manner as the above-mentioned physical quantities, viz. ultrasound propagation velocity and electrical conductivity, to construct a set of points.

Those measurements are performed in triplicate for each lot and the mean results are used to provide accurate data.

The inventors of the present invention discovered that by interconnecting the points of the lots in which the amount of each water and hydrogen fluoride is constant, there is obtained a correlation between the two physical quantities at a given temperature. The curves thus obtained form a mutually generally stripe pattern like parallel pattern.

When, in said ternary mixture, the concentration of water is 4.0 to 24 weight % and that of hydrogen fluoride is 2.0 to 10 weight %, with sulfuric acid accounting for the remainder, the preferred physical quantities to be measured are temperature, ultrasound propagation velocity, and electrical conductivity. On the other hand, when, in said ternary mixture, the concentration of water is 0 to 7.0 weight % and that of hydrogen fluoride is 0 to 9.0 weight %, with sulfuric acid accounting for the remainder, viscosity instead of electrical conductivity is a preferred physical quantity to be measured. Therefore, the physical quantities to be measured can be judiciously selected according to the predicted concentration ranges of the respective components in the ternary mixture to be analyzed and a decision can be made on whether temperature, ultrasound propagation velocity, and electrical conductivity should be chosen or temperature, ultrasound propagation velocity, and viscosity should be chosen as the quantities to be measured.

Now, the procedure of determining the concentration of each component in a ternary mixture of unknown component concentrations by utilizing the above constructed calibration curves is described.

The sample to be measured is a ternary mixture the concentration of which is unknown for any of its three components. Using this sample, ultrasound propagation velocity is measured at a given constant temperature. Then, electrical conductivity is measured for the same sample at the same temperature. The measured ultrasound propagation velocity and electrical conductivity values are topologically identified as the point of intersection of the horizontal and vertical axes on the graph of calibration curves constructed as above.

When the position thus identified lies on any of the calibration curves constructed as above or coincides with any point of intersection of the curves, the particular concentration of water and/or hydrogen fluoride represents the concentration of water and/or hydrogen fluoride of the sample. When the position of the point found is not on any of said calibration curves or coincide with any point of intersection of the curves, the concentration of water and/or hydrogen fluoride of the sample can be estimated by proportional approximation from the relation of distances of said point from the generally parallel two calibration curves. For example, when the particular point is situated between the calibration curve for water concentration=10 weight % and the calibration curve for water concentration=11 weight % and [the distance between the two calibration curves]:[the distance between the point and the calibration curve for 10 weight % water]=10:4, the water concentration of the sample is found to be 10.4 weight %. The concentration of hydrogen fluoride can also be determined in the same manner as the concentration of water. The concentration of sulfuric acid can be found as the remainder after subtraction of the concentration of water and hydrogen fluoride combined from 100 weight %.

The procedure of determining concentrations on the calibration curves by proportional approximation has been just described with respect to concentration but the same principle applies to the determination of temperatures as well.

By identifying a point of intersection on a graph of calibration curves constructed from measured values of two physical quantities at a given temperature in the above manner and finding the topological relation of said point with the calibration curves, the concentrations of water, hydrogen fluoride and sulfuric acid in the sample can be determined.

In accordance with the component concentration determination method of the invention, once the above-mentioned calibration curves are constructed, the concentrations of water, hydrogen fluoride and sulfuric acid in a sample can be easily determined by measuring the ultrasound propagation velocity and either electrical conductivity or viscosity of the sample at a given temperature.

Therefore, a typical embodiment of the equipment for use in the component concentration determination method of the invention comprises ① a means for maintaining a sample at a given constant temperature, ② a means for measuring ultrasound propagation velocity, ③ a means for measuring electrical conductivity or viscosity, and ④ a means (hereinafter referred to as means (M1)) for determining the concentrations of water, hydrogen fluoride, and sulfuric acid in the sample from the measured values generated by said means ② and ③ using the calibration curves as described above. Although the means ④ may be a manual means employing said graph of calibration curves, an automatic mode of data processing with a computer which will be described hereinafter in the Examples is preferred because of its accurate and rapid processing. Then, by causing a conventional automatic flow control valve to be driven according to the information output from the computer, the supply of sulfuric anhydride can be automatically controlled.

The process of the invention for continuous production of hydrogen fluoride comprising the use of the above-described component concentration determination method for a ternary mixture is now described in detail.

The process of the invention for continuous production of hydrogen fluoride applies the above component concentration determination method of the invention to determination of the concentration of water in the high-boiling mixture (b) available in the conventional process for continuous production of hydrogen fluoride as described under the heading of Prior Art.

In the process of the invention for continuous production of hydrogen fluoride, hydrogen fluoride is produced by the following steps, viz. feeding the crude gas available from kneading and heating stage of starting fluorspar-sulfuric acid to a crude gas washing column, in which the crude gas is washed by serial contact with the high-boiling mixture composed predominantly of sulfuric acid and hydrogen fluoride, withdrawing a low-boiling mixture composed predominantly of hydrogen fluoride from the top of said crude gas washing column for said washing, and the high-boiling mixture composed predominantly of sulfuric acid and containing minor proportions of water and hydrogen fluoride as accumulated in the bottom of said crude gas washing column is withdrawn, and an approximately equivalent amount of sulfuric anhydride, based on the amount of water occurring in said high-boiling mixture is supplied thereto, to form sulfuric acid. The sulfuric anhydride mentioned above can be usually supplied in the form of fuming sulfuric acid so as to provide a mixture of sulfuric anhydride and sulfuric acid.

In accordance with the present invention, the amount of water occurring in said high-boiling mixture is determined by application of the above-described component concentration determination method or means of the invention. And, sulfuric anhydride is added according to the result of determination. In this manner, the invention enables a real-time determination of the amount of water serially at desired time intervals or continuously without resort to any manual operation and insures a rapid, safe supply and blending of the optimum amount of sulfuric anhydride at any time.

In the process of the invention, sulfuric anhydride is supplied in a stoichiometrically sufficient amount to form sulfuric acid on reaction with water according to the amount of water in said high-boiling mixture (b) as determined by the above method. The means for this supply of sulfuric anhydride [hereinafter referred to as means (M2)] is not particularly restricted only provided that sulfuric anhydride can be supplied thereby in said stoichiometrically equivalent amount based on the amount of water in high-boiling mixture (b) as measured by said means (M1). Thus, the means may be a manual means or an automatic means. The preferred means (M2) is such that the amount of sulfuric anhydride is automatically adjusted in response to the amount of water in high-boiling mixture (b) as detected by said means (M1).

Furthermore, in the present invention, said means (M2) is preferably controlled by a means capable of determining the necessary feeding amount of sulfuric anhydride according to the result of measurement by said means (M1) and data processing. Such a control means may for example be a computer which calculates said stoichiometrically equivalent amount of sulfuric anhydride from the water concentration data generated by said means (M1).

The above measurement by means (M1) and conversion can be performed prior to blending of sulfuric anhydride with said high-boiling mixture (b) or after the blending, or even before and after the blending of sulfuric anhydride with the high-boiling mixture but from the standpoint of insuring the optimum control of sulfuric acid concentration during the production process, it is preferably carried out before and after the blending of sulfuric anhydride with said high-boiling mixture.

In the present invention, the amount of sulfuric anhydride to be added to said high-boiling mixture is preferably more or less equivalent to the amount required for forming sulfuric acid through reaction with the water occurring in said high-boiling mixture. If the amount of sulfuric anhydride is less than said equivalent amount necessary for the formation of sulfuric acid through reaction with the water contained in said high-boiling mixture, some of the water remains unreacted to reduce the reaction rate, with the consequence that the reaction mixture tends to undergo caking or form deposits on the internal wall of the equipment to interfere with undeterred progress of the reaction between the feed sulfuric acid and fluorspar and accelerate corrosion of the equipment and pipes associated with the recycling process, inclusive of the kiln and crude gas washing column.

Thus, the inventors of the present invention confirmed empirically that in order that the reaction rate of fluorspar with sulfuric acid may be maintained at a high level and caking of the reaction mixture may be prevented, the amount of water in the sulfuric acid feed must be controlled at a concentration not higher than about 5 weight %, preferably about 3 weight % or less. In accordance with the invention, the amount of water in the sulfuric acid feed can be maintained at 3 weight % or less at all times by adding sulfuric anhydride to the high-boiling mixture available from the crude gas washing column in a substantially stoichiometric amount, that is to say the amount necessary to form sulfuric acid through reaction with the water contained in said mixture.

In the present invention, by measuring the amount of water contained in said high-boiling mixture (b) and supplying the necessary amount of sulfuric anhydride as described above, it is possible to avoid the risk for the excess of water with respect to said sulfuric anhydride remaining unreacted in the feed sulfuric acid to interfere with smooth progress of the reaction of sulfuric acid with fluorspar and the risk for accelerated corrosion of the equipment and pipeline associated with the recycling process. Furthermore, it is also possible to avoid the risk of supplying an excess of sulfuric anhydride with respect to said water to increase the contaminant sulfuric acid content of the product hydrogen fluoride.

The present invention includes a step of supplying a supplemental amount of sulfuric acid for providing the necessary amount of sulfuric acid for reaction with the feed fluorspar. In this step, also, the concentration of water can be determined by the above-described method for the purpose of confirming or adjusting the concentration of water.

BEST MODE FOR CARRYING OUT THE INVENTION

The following examples illustrate the present invention in further detail but are by no means limitative of the scope of the invention.

REFERENCE EXAMPLE 1

Construction of calibration curves representing the correlation between the concentration of each component of a ternary mixture comprising sulfuric acid, hydrogen fluoride, and water and the following three physical quantities.

REFERENCE EXAMPLE 1-1

When the three physical quantities are temperature, ultrasound propagation velocity, and electrical conductivity:

Using the procedure described hereinbefore, sample ternary mixtures of water, hydrogen fluoride, and sulfuric acid varying in the concentrations of the respective components were prepared as follows.

By varying the concentration of water at 2.0 weight % intervals over the range of 4.0 to 24.0 weight % and the concentration of hydrogen fluoride at 1.0 weight % intervals over the range of 2.0 to 10.0 weight %, with sulfuric acid invariably accounting for the remainder, 90 different samples, each in triplicate, were prepared (a total of 270 samples).

Each of the above samples was placed in an acid-resistant vessel or cell maintained at 40° C. and the determination of ultrasound propagation velocity (Ultrasonic Industrial Co., UVM-2 type, 2 MHz) and electrical conductivity (a conductivity meter) was carried out and the mean of triplicate was calculated. The results are presented in Table 1. In Table 1, the values in the upper row represent ultrasound propagation velocity (m/s) and the values in the lower row represent electrical conductivity (mS/cm).

Figure 1:
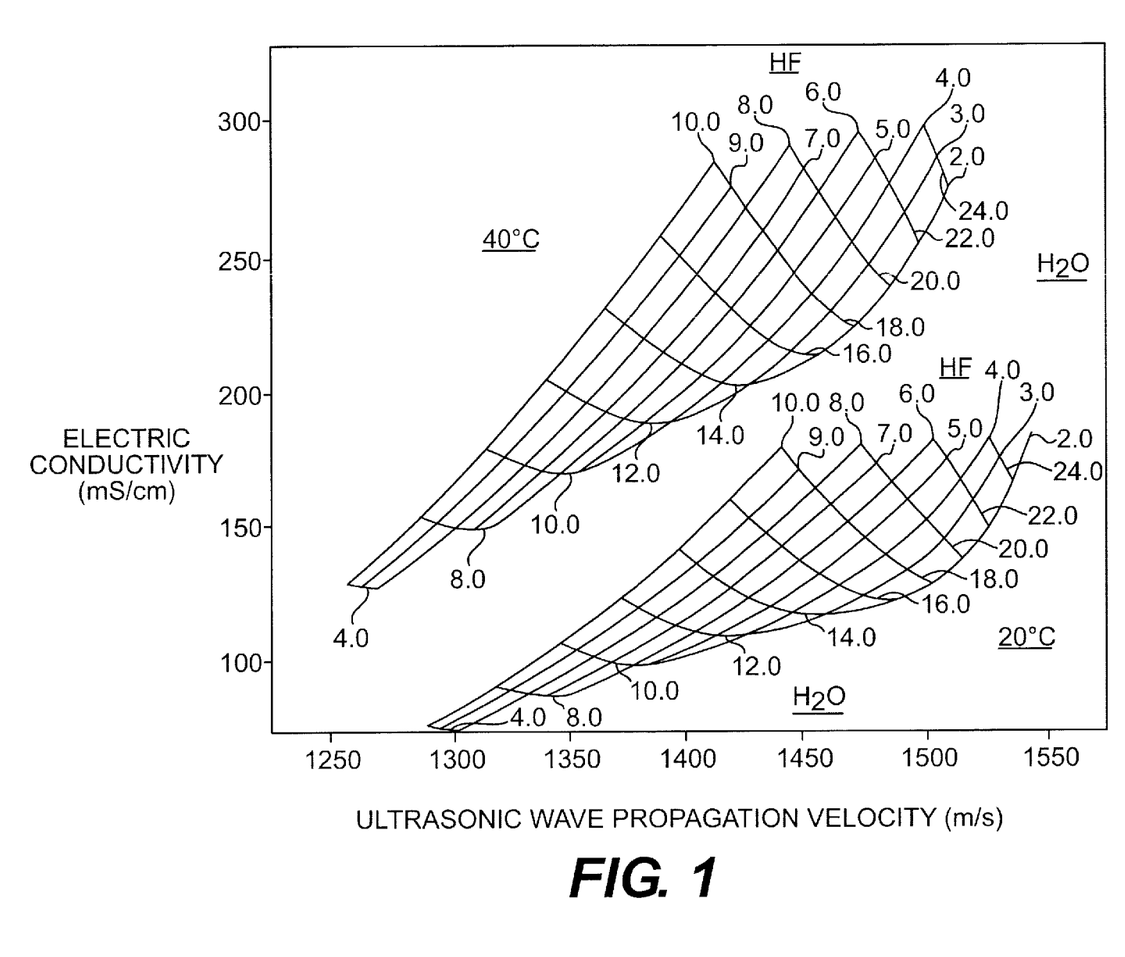
FIG. 1 is a graph showing the calibration curves of the invention as constructed in Reference Example 1-1, which represent the relationships of the concentrations of components of a ternary mixture of sulfuric acid, hydrogen fluoride and water, within certain respective concentration ranges, with ultrasound propagation velocity (m/s) and electrical conductivity (mS/cm) at 20° C. and 40° C. The upper set of calibration curves corresponds to 40° C. and the lower set of calibration curves corresponds to 20° C. The values given to the respective calibration curves are the concentrations (weight %) of water and the concentrations (weight %) of hydrogen fluoride.

The measured values at each temperature were plotted on a graph with ultrasound propagation velocity on the horizontal axis and electrical conductivity on the vertical axis as shown in FIG. 1. The values for which no correlation could be obtained were not plotted (not entered in Table 1, either).

The above procedure was repeated except that a measuring temperature of 20° C. was used. The results are presented in Table 2 and FIG. 1.

Figure 2:
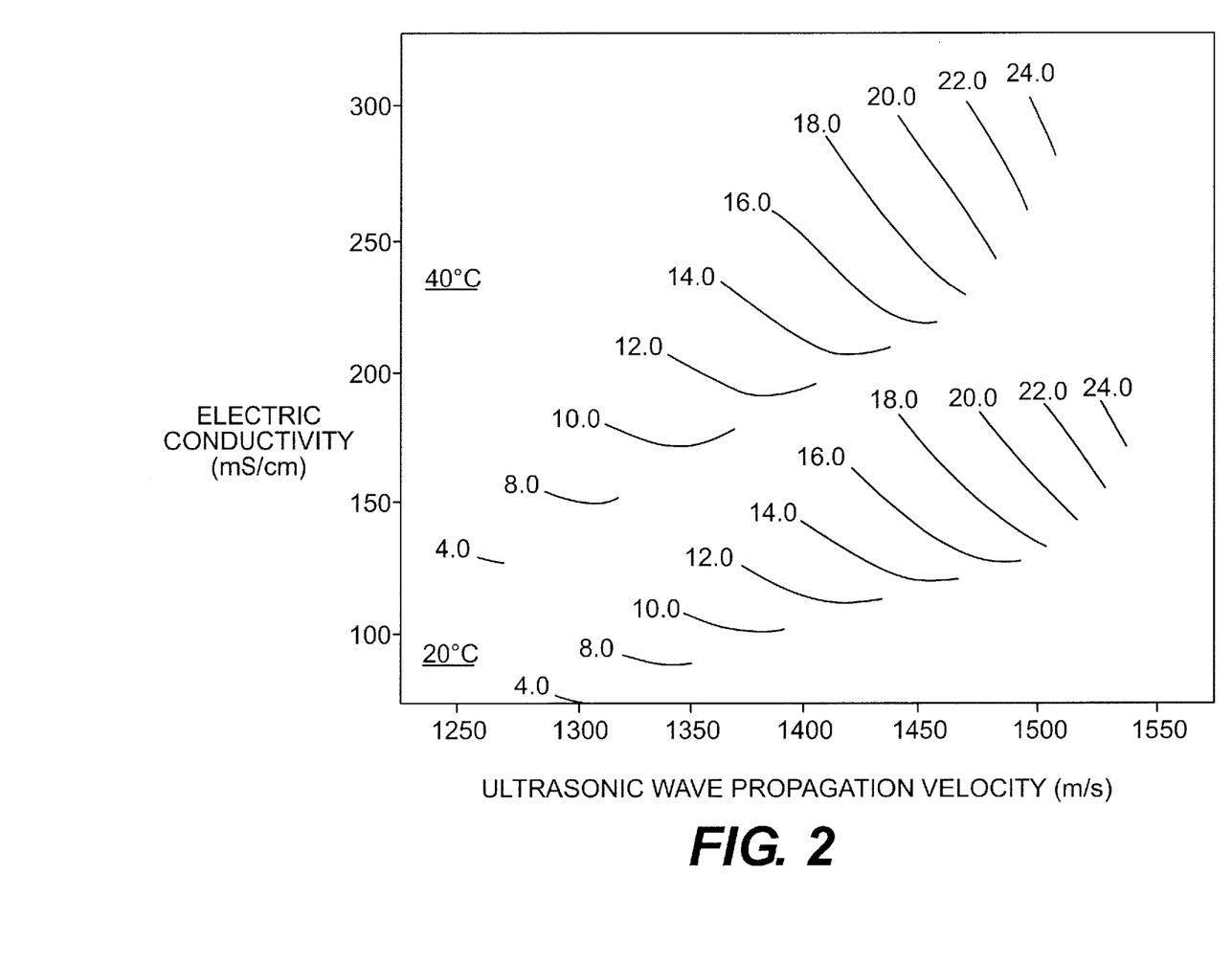
FIG. 2 is a graph available upon erasure of the calibration curves for hydrogen fluoride from FIG. 1 for the ease of determination of water concentration.

FIG. 2 was obtained upon partial erasure of the image of FIG. 1 leaving only the calibration curves representing the concentration of water for convenience's sake.

REFERENCE EXAMPLE 1-2

When the three physical quantities are temperature, ultrasound propagation velocity, and viscosity:

The following samples were prepared by the same procedure as used in Reference Example 1-1.

By varying the concentration of water at intervals of 1.0 weight % over the range of 0.0 to 7.0 weight % and the concentration of hydrogen fluoride at 1.0 weight % intervals over the range of 0.0 to 9.0 weight %, with sulfuric acid invariably accounting for the remainder, 80 kinds of samples were prepared in triplicate (a total of 240 samples).

Each of the above samples was placed in an acid-resistant vessel or cell maintained at 40° C. and subjected to the determination of ultrasound propagation velocity (Ultrasonic Industrial Co., UVM-2 type, 2 MHz) and viscosity (a viscometer). The mean of triplicate was calculated for use as the measured value for each kind of sample. The results are presented in Table 3. In the table, the values in the upper row represent ultrasound propagation velocity (m/s) and the values in the lower row represent viscosity (cP).

Figure 3:
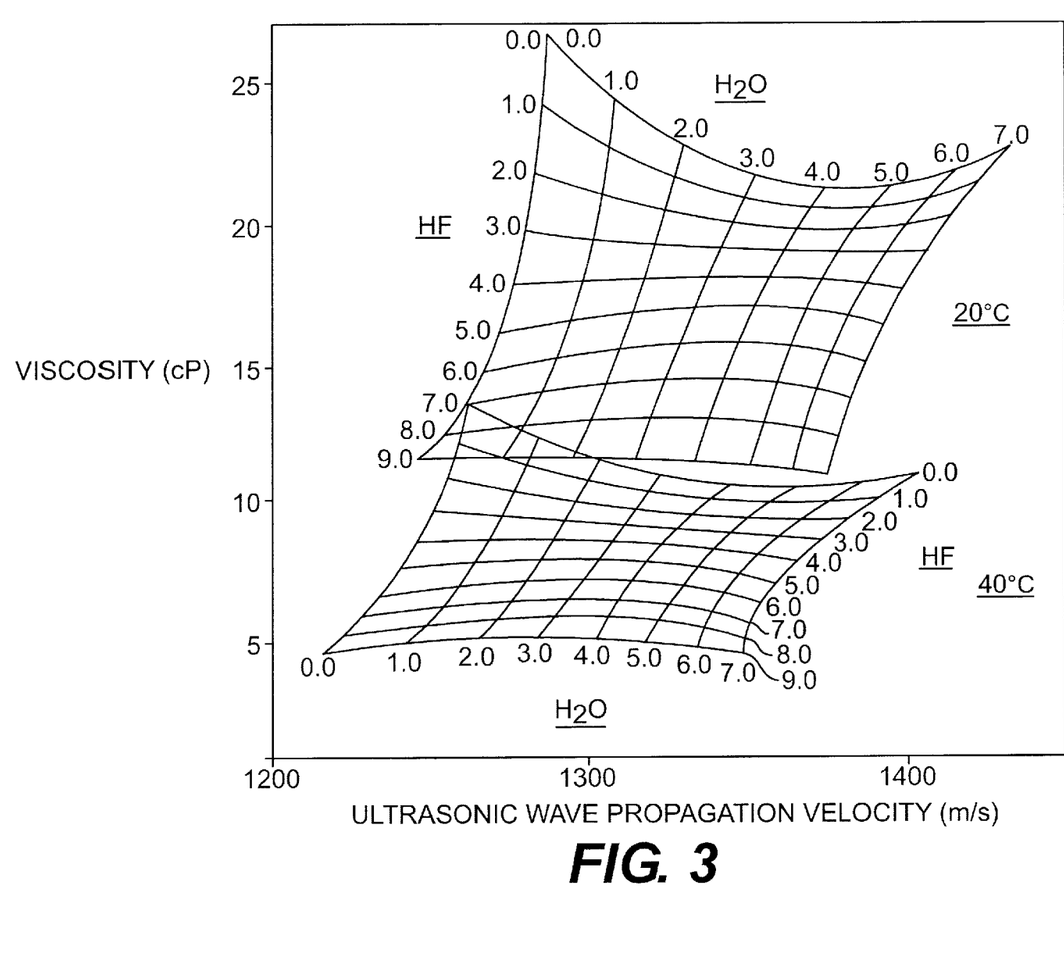
FIG. 3 is a graph showing the calibration curves of the invention as constructed in Reference Example 1-2, which represent the relationships of the concentrations of components of a ternary mixture of sulfuric acid, hydrogen fluoride, and water, within certain respective concentration ranges, with ultrasound propagation velocity (m/s) and viscosity (cP) at 20° C. and 40° C. The upper set of calibration curves represent 20° C. and the lower set of calibration curves represent 40° C. The values given to the respective calibration curves are the concentrations of water (weight %) and the concentrations of hydrogen fluoride (weight %).

Those measured values at each temperature were plotted on a graph with ultrasound propagation velocity on the horizontal axis and viscosity on the vertical axis as shown in FIG. 3.

The above procedure was repeated except that a measuring temperature of 20° C. was used. The results are presented in Table 4 and FIG. 3.

Figure 4:
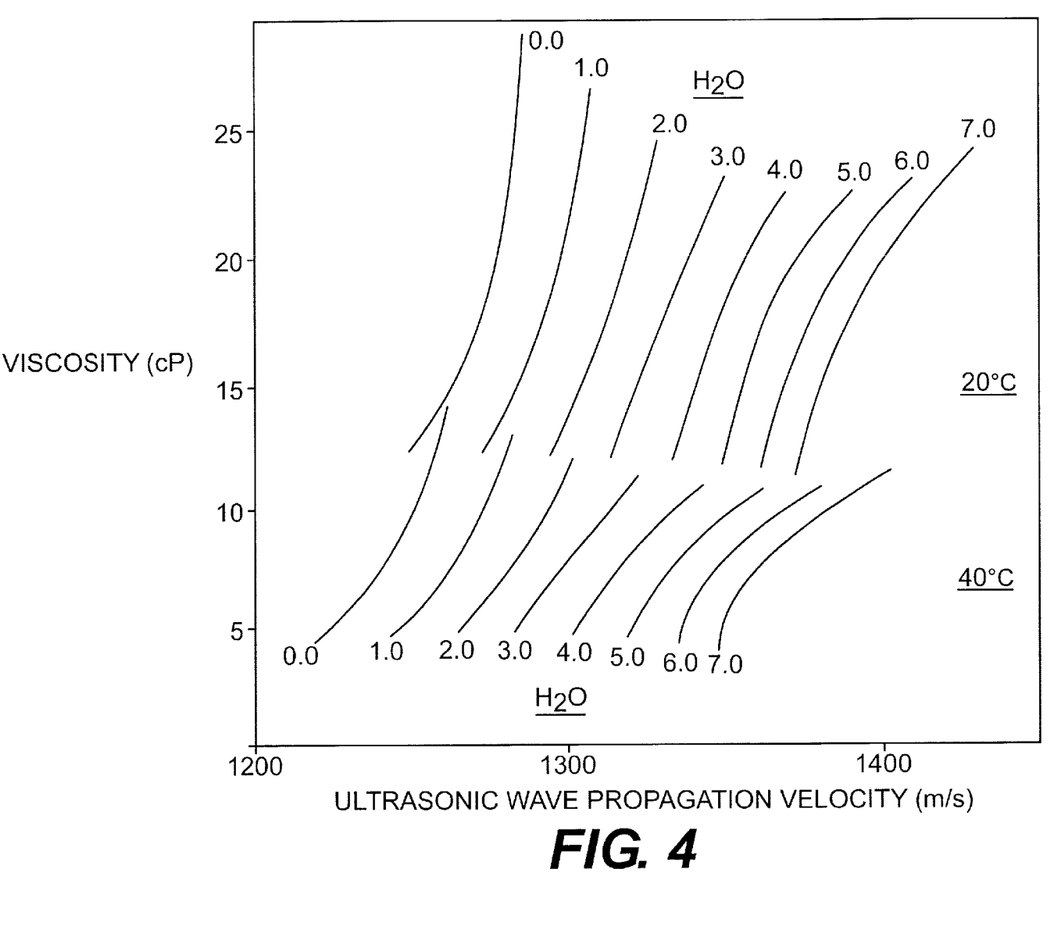
FIG. 4 is a graph available upon erasure of the calibration curves for hydrogen fluoride from FIG. 3 for the ease of determination of water concentration.

FIG. 4 was obtained upon partial erasure of the image of FIG. 3 leaving only the calibration curves for the concentration of water.

TABLE 1

| | | Concentration of Hydrogen Fluoride (weight %) | | | | | | | | |
|---|---|---|---|---|---|---|---|---|---|---|
| | | 2 | 3 | 4 | 5 | 6 | 7 | 8 | 9 | 10 |
| Concentration of Water (weight %) | 4 | — | — | — | — | — | — | 1266.8 | 1260.2 | 1255.0 |
| | | — | — | — | — | — | — | 126.7 | 127.8 | 129.0 |
| | 8 | — | — | — | — | 1308.8 | 1306.3 | 1297.5 | 1290.6 | 1283.8 |
| | | — | — | — | — | 149.7 | 149.5 | 150.6 | 152.3 | 154.0 |
| | 10 | — | — | 1363.8 | 1352.5 | 1342.5 | 1333.8 | 1326.3 | 1318.8 | 1311.3 |
| | | — | — | 176.1 | 171.6 | 169.9 | 171.3 | 175.0 | 175.6 | 179.0 |
| | 12 | — | — | 1340.0 | 1328.8 | 1369.4 | 1361.7 | 1354.0 | 1344.4 | 1336.3 |
| | | — | — | 192.0 | 189.0 | 191.5 | 194.6 | 197.3 | 201.1 | 205.1 |
| | 14 | — | 1450.0 | 1411.3 | 1403.1 | 1394.4 | 1386.3 | 1378.4 | 1369.4 | 1361.1 |
| | | — | 202.8 | 204.8 | 206.6 | 210.6 | 215.6 | 221.0 | 225.6 | 230.7 |
| | 16 | 1455.0 | 1442.5 | 1432.5 | 1423.8 | 1415.5 | 1409.4 | 1400.9 | 1392.5 | 1383.8 |
| | | 215.0 | 216.1 | 219.9 | 225.6 | 231.3 | 238.1 | 244.9 | 252.0 | 258.5 |
| | 18 | 1468.1 | 1458.4 | 1450.1 | 1443.4 | 1435.8 | 1427.5 | 1421.3 | 1413.8 | 1406.3 |
| | | 225.0 | 230.8 | 236.9 | 246.1 | 254.0 | 260.8 | 263.6 | 276.9 | 286.4 |
| | 20 | 1483.5 | 1473.8 | 1467.5 | 1459.6 | 1453.5 | 1445.0 | 1438.8 | — | — |
| | | 238.9 | 248.1 | 256.9 | 265.7 | 275.0 | 283.2 | 291.5 | — | — |
| | 22 | 1493.8 | 1487.5 | 1481.9 | 1475.6 | 1468.8 | — | — | — | — |
| | | 255.5 | 266.7 | 277.2 | 286.9 | 296.0 | — | — | — | — |
| | 24 | 1503.8 | 1499.0 | 1492.7 | — | — | — | — | — | — |
| | | 276.3 | 287.7 | 299.2 | — | — | — | — | — | — |

TABLE 2

| | | Concentration of Hydrogen Fluoride (weight %) | | | | | | | | |
|---|---|---|---|---|---|---|---|---|---|---|
| | | 2 | 3 | 4 | 5 | 6 | 7 | 8 | 9 | 10 |
| Concentration of Water (weight %) | 4 | — | — | — | — | — | — | 1300.2 | 1293.8 | 1292.4 |
| | | — | — | — | — | — | — | 75.0 | 76.0 | 77.2 |
| | 8 | — | — | — | — | 1337.4 | 1337.2 | 1329.8 | 1325.1 | 1316.9 |
| | | — | — | — | — | 88.6 | 89.1 | 89.2 | 90.3 | 98.0 |
| | 10 | — | — | 1400.2 | 1384.5 | 1376.5 | 1366.1 | 1359.8 | 1352.2 | 1343.0 |
| | | — | — | 100.5 | 100.1 | 100.0 | 101.8 | 103.2 | 105.1 | 107.4 |
| | 12 | — | — | 1421.7 | 1410.7 | 1402.4 | 1384.5 | 1378.0 | 1378.0 | 1370.0 |
| | | — | — | 110.9 | 110.8 | 112.5 | 114.4 | 116.5 | 120.5 | 125.2 |
| | 14 | 1459.5 | 1454.8 | 1444.0 | 1433.3 | 1426.2 | 1417.9 | 1409.8 | 1402.3 | 1394.5 |

TABLE 2-continued

| | | Concentration of Hydrogen Fluoride (weight %) | | | | | | | |
|---|---|---|---|---|---|---|---|---|---|
| | | 2 | 3 | 4 | 5 | 6 | 7 | 8 | 9 | 10 |
| | | 118.2 | 117.8 | 119.3 | 121.0 | 125.1 | 129.1 | 133.0 | 133.8 | 141.8 |
| | 16 | 1485.7 | 1473.8 | 1464.9 | 1453.8 | 1445.7 | 1439.1 | 1430.5 | 1425.0 | 1417.0 |
| | | 122.7 | 125.2 | 129.0 | 132.6 | 138.4 | 143.8 | 148.8 | 154.6 | 160.8 |
| | 18 | 1499.8 | 1490.5 | 1481.0 | 1474.6 | 1467.3 | 1460.4 | 1453.4 | 1445.7 | 1437.7 |
| | | 129.3 | 134.7 | 140.3 | 146.6 | 152.8 | 158.5 | 164.9 | 172.3 | 179.7 |
| | 20 | 1512.5 | 1504.4 | 1497.6 | 1489.9 | 1483.7 | 1476.8 | 1471.1 | — | — |
| | | 139.2 | 146.0 | 153.2 | 160.5 | 166.8 | 175.3 | 181.1 | — | — |
| | 22 | 1523.2 | 1516.1 | 1510.8 | 1504.2 | 1499.2 | — | — | — | — |
| | | 151.7 | 160.5 | 167.6 | 175.9 | 182.8 | — | — | — | — |
| | 24 | 1532.3 | 1526.8 | 1521.4 | — | — | — | — | — | — |
| | | 166.7 | 176.7 | 184.3 | — | — | — | — | — | — |

TABLE 3

| | | Concentration of Water (weight %) | | | | | | | |
|---|---|---|---|---|---|---|---|---|
| | | 0 | 1 | 2 | 3 | 4 | 5 | 6 | 7 |
| Concentration of Hydrgen Fluoride (weight %) | 0 | 1282.9 | 1305.7 | 1327.9 | 1349.6 | 1369.6 | 1389.0 | 1408.3 | 1428.3 |
| | | 13.54 | 12.31 | 11.34 | 10.69 | 10.39 | 10.33 | 10.46 | 10.91 |
| | 1 | 1282.1 | 1303.8 | 1325.4 | 1345.8 | 1365.8 | 1384.2 | 1401.7 | 1417.9 |
| | | 12.04 | 11.37 | 10.59 | 10.16 | 9.92 | 9.84 | 9.85 | 10.00 |
| | 2 | 1279.8 | 1301.0 | 1322.3 | 1343.0 | 1361.7 | 1378.3 | 1395.0 | 1409.5 |
| | | 10.74 | 10.31 | 9.92 | 9.54 | 9.43 | 9.28 | 9.12 | 9.21 |
| | 3 | 1276.5 | 1298.9 | 1319.6 | 1339.2 | 1357.7 | 1372.6 | 1389.2 | 1401.7 |
| | | 9.62 | 9.49 | 9.17 | 9.08 | 8.88 | 8.70 | 8.57 | 8.39 |
| | 4 | 1272.5 | 1295.8 | 1316.3 | 1335.0 | 1354.0 | 1368.4 | 1382.5 | 1394.6 |
| | | 8.49 | 8.54 | 8.47 | 8.31 | 8.27 | 8.14 | 7.84 | 7.66 |
| | 5 | 1268.2 | 1292.1 | 1312.5 | 1332.1 | 1349.5 | 1363.8 | 1377.5 | 1388.3 |
| | | 7.52 | 7.71 | 7.79 | 7.77 | 7.70 | 7.54 | 7.19 | 6.96 |
| | 6 | 1263.2 | 1288.3 | 1308.5 | 1327.7 | 1344.8 | 1359.2 | 1373.3 | 1382.9 |
| | | 6.58 | 6.87 | 7.02 | 7.11 | 7.10 | 6.84 | 6.57 | 6.18 |
| | 7 | 1256.8 | 1281.6 | 1304.2 | 1323.6 | 1341.1 | 1355.4 | 1368.3 | 1378.7 |
| | | 5.85 | 6.11 | 6.33 | 6.42 | 6.40 | 6.21 | 5.89 | 5.63 |
| | 8 | 1250.8 | 1275.8 | 1299.7 | 1318.3 | 1337.1 | 1351.7 | 1364.2 | 1375.8 |
| | | 5.14 | 5.48 | 5.67 | 5.75 | 5.70 | 5.56 | 5.34 | 4.99 |
| | 9 | 1244.7 | 1269.8 | 1294.9 | 1313.8 | 1333.3 | 1348.7 | 1362.1 | 1372.1 |
| | | 4.65 | 4.87 | 5.01 | 5.08 | 5.00 | 5.10 | 4.68 | 4.47 |

TABLE 4

| | | Concentration of Water (weight %) | | | | | | | |
|---|---|---|---|---|---|---|---|---|
| | | 0 | 1 | 2 | 3 | 4 | 5 | 6 | 7 |
| Concentration of Hydrogen Fluoride (weight %) | 0 | 1259.2 | 1281.3 | 1302.5 | 1322.9 | 1343.3 | 1362.5 | 1383.3 | 1402.9 |
| | | 26.61 | 24.40 | 22.89 | 21.73 | 21.13 | 21.18 | 21.68 | 22.71 |
| | 1 | 1255.8 | 1277.5 | 1299.2 | 1319.6 | 1338.8 | 1357.1 | 1373.3 | 1391.7 |
| | | 24.14 | 22.75 | 21.67 | 20.96 | 20.54 | 20.55 | 20.90 | 21.51 |
| | 2 | 1252.5 | 1275.0 | 1295.0 | 1315.8 | 1333.8 | 1350.0 | 1365.4 | 1380.0 |
| | | 21.69 | 21.08 | 20.50 | 20.05 | 19.84 | 19.86 | 19.93 | 20.28 |
| | 3 | 1248.8 | 1270.4 | 1292.5 | 1311.3 | 1327.9 | 1345.0 | 1358.3 | 1371.7 |
| | | 19.78 | 19.48 | 19.29 | 19.13 | 19.10 | 18.99 | 18.99 | 18.99 |
| | 4 | 1244.2 | 1266.3 | 1288.3 | 1305.8 | 1324.0 | 1339.6 | 1352.1 | 1365.8 |
| | | 17.82 | 17.92 | 17.99 | 18.08 | 18.02 | 18.00 | 17.85 | 16.37 |
| | 5 | 1238.8 | 1262.5 | 1283.3 | 1302.3 | 1318.9 | 1335.0 | 1346.7 | 1359.2 |
| | | 16.11 | 16.54 | 16.78 | 16.89 | 17.01 | 16.93 | 16.71 | 16.38 |
| | 6 | 1234.2 | 1357.6 | 1278.3 | 1298.7 | 1315.4 | 1330.8 | 1342.1 | 1353.8 |
| | | 14.32 | 15.16 | 15.47 | 15.68 | 15.70 | 15.62 | 15.41 | 15.01 |
| | 7 | 1232.5 | 1251.7 | 1274.2 | 1293.7 | 1310.4 | 1327.0 | 1338.7 | 1350.0 |
| | | 13.46 | 13.91 | 14.20 | 14.35 | 14.35 | 14.30 | 14.05 | 13.62 |

TABLE 4-continued

| | Concentration of Water (weight %) | | | | | | | |
|---|---|---|---|---|---|---|---|---|
| | 0 | 1 | 2 | 3 | 4 | 5 | 6 | 7 |
| 8 | 1222.1 | 1246.7 | 1268.3 | 1389.2 | 1306.3 | 1322.9 | 1336.7 | 1348.7 |
| | 12.38 | 12.72 | 12.86 | 12.89 | 12.89 | 12.75 | 12.55 | 12.17 |
| 9 | 1215.0 | 1240.0 | 1263.3 | 1283.9 | 1302.8 | 1320.1 | 1334.6 | 1348.6 |
| | 11.53 | 11.57 | 11.50 | 11.41 | 11.31 | 11.19 | 11.04 | 10.78 |

EXAMPLE 1

Determination of the concentration of water in a ternary mixture comprising sulfuric acid, hydrogen fluoride, and water by using the calibration curves constructed in Reference Example 1.

EXAMPLE 1-1

When the calibration curves shown in FIG. 1 were used:

The concentration of water in a mixed acid comprising hydrogen fluoride and sulfuric acid was measured at 40° C. The samples shown in Table 1 were prepared by varying the concentration of sulfuric acid in the mixed acid over the range of 73 to 86 weight % and the concentration of hydrogen fluoride over the range of 2 to 10 weight %, with water invariably accounting for the remainder. The determination of ultrasound propagation velocity (m/s) and electrical conductivity (mS/cm) was respectively carried out twice for each sample and the mean of it was calculated. By reference to the calibration curves shown in FIG. 1, the mean values were converted manually to the concentration of water. The results are presented in Table 5.

It was found from Table 5 that the concentration of water could be determined with high precision by the method of the invention. The values in parentheses in Table 5 are the actual weight % values of water.

EXAMPLE 1-2

When the calibration curves shown in FIG. 3 were used:

Using sample mixtures of sulfuric acid, hydrogen fluoride, and water (in parentheses) varying in concentration as in Table 6, the determination of ultrasound propagation velocity (m/s) and viscosity (cP) was carried out at 20° C. by the same procedure as in Example 1-1. The determinations were respectively carried out twice for each sample and the mean of it was calculated. With reference to the calibration curves imaged in FIG. 3, the measured values were manually converted to the concentration of water as described hereinbefore. The results are presented in Table 6. As it was the case with Table 5, it was found from Table 6 that the concentration of water can be determined with high precision.

TABLE 5

| | | Sulfuric acid (weight %) | | | | | |
|---|---|---|---|---|---|---|---|
| | | 73 | 75 | 78 | 81 | 84 | 86 |
| Hydrogen Fluoride (weight %) | 10 | 271 1394.4 | 240 1368.1 | 198 1328.8 | 163 1293.7 | — | — |
| | | 16.9 (17) | 14.6 (15) | 11.5 (12) | 8.7 (9) | | |
| | 7 | 279 1443.1 | 254 1423.1 | 223 1393.7 | 185 1351.9 | 153 1313.8 | — |
| | | 19.5 (20) | 17.4 (18) | 14.6 (15) | 11.2 (12) | 8.6 (9) | |
| | 4 | 290 1487.2 | 259 1462.2 | 231 1443.2 | 210 1417.7 | 187 1384.8 | 174 1359.2 |
| | | 23.1 (23) | 20.2 (21) | 17.3 (18) | 14.6 (15) | 11.8 (12) | 9.8 (12) |
| | 2 | — | 261 1496.3 | 238 1479.3 | 224 1465.2 | — | — |
| | | | 22.5 (23) | 19.7 (20) | 17.7 (17) | | |

Ultrasound propagation velocity (m/s)
Conductivity (mS/cm)
Water (weight %)

TABLE 6

| | | Sulfuric acid (weight %) | | | | |
|---|---|---|---|---|---|---|
| | | 86 | 89 | 92 | 95 | 97 |
| Hydrogen Floride weight % | 8 | 5.31 1369.4 | 5.65 1263.5 | — | — | — |
| | | 5.9 (6) | 2.7 (3) | | | |
| | 6 | — | 6.73 1364.7 | 7.01 1262.4 | — | — |
| | | | 5.2 (5) | 2.1 (2) | | |
| | 4 | — | 7.71 1425.3 | 8.27 1344.2 | 8.55 1236.5 | - |

TABLE 6-continued

| | Sulfuric acid (weight %) | | | | |
|---|---|---|---|---|---|
| | 86 | 89 | 92 | 95 | 97 |
| 2 | — | 6.9 (7) — 6.0 (6) | 3.9 (4) 9.19 1431.8 | 1.1 (1) 9.69 1318.8 2.7 (3) | 10.33 1244.7 0.9 (1) |

Ultrasound progagation velocity (m/s)
Viscosity (weight %)
Water (weight %)

EXAMPLE 2

Process for Continuous Production of Hydrogen Fluoride

The equipment illustrated in FIG. 5 was used.

Pulverized fluorspar was fed to a kneader 1 through the duct 11. The starting sulfuric acid was introduced into the kneader 1 through the duct 12 and 13. In the kneader 1, the feed fluorspar and sulfuric acid were mixed and the reaction began. This reaction mixture was transferred to a kiln 2 disposed immediately downstreams, in which the reaction was accelerated by heating at about 400 to 500° C. to produce a crude gas containing the three components, viz. unreacted sulfuric acid feed (A), reaction product hydrogen fluoride (B), and water produced by reaction of the trace impurity in fluorspar feed (C). This crude gas entrained the various solid particles (d) produced by the reaction as dust.

The above crude gas generated in the kneader 1 and kiln 2 was introduced into the bottom of a crude gas washing column 3 through the duct 14 and washed with hydrogen fluoride introduced from the top of the column. This washing with hydrogen fluoride was carried out by withdrawing the reaction product, hydrogen fluoride which is obtained from the crude gas washing column 3, from that to a condenser via the duct 18 and condensing a portion of it by cooling and returning the condensed hydrogen fluoride to the crude gas washing column 3 via the duct 17.

As the above crude gas was cooled in the course of washing in the crude gas washing column 3, a high-boiling mixture (b) composed predominantly of sulfuric acid (A) and containing minor proportions of hydrogen fluoride (B) and water (C) was liquefied, fell into the bottom of the crude gas washing column 3, and was pooled in a reservoir tank 4. A low-boiling mixture (a) composed predominantly of the product hydrogen fluoride, which remained after separation of said high-boiling mixture (b), was recovered through the duct 18. The low-boiling mixture (a) thus recovered contained, in addition to hydrogen-fluoride, various low-boiling gaseous components such as $SiF_4$, $SO_2$, and $CO_2$. Therefore, this fraction was further purified by known purification procedures to provide high-purity hydrogen fluoride.

The high-boiling mixture (b) pooled in the reservoir tank 4 was fed to the recycling process by a pump 22 disposed in the reservoir tank 4 through the duct 15. In this operation, a flow control valve 23 provided in the duct 15 was controlled in such a manner that a portion of (b) is fed through the duct 24 to crude gas washing column 3 at a level below its middle portion and showered into contact with the ascending high-temperature crude gas. By this contact, the dust (D) occurring in an appreciable amount in the crude gas is trapped and recovered in the reservoir tank 4. At the same time, said high-boiling mixture (b) in the reservoir tank 4 was introduced into a mixing tank 5 through lines 15 and 25. On the other hand, the concentration of said water (C) contained in said high-boiling mixture (b) was determined by means (M1) and the necessary amount of sulfuric anhydride (B) was fed by means (M2) to the mixing tank 5 via the duct 16. In addition, fresh sulfuric acid was separately fed to the mixing tank 5 via the duct 12 after control of its flow rate by a flow control valve 26.

As means M1 (19), Fuji Industrial's Model-50 was used and as means M1 (20), Fuji Industrial's Model-70 was used. The latter means was used primarily for checking whether the concentration of water was appropriate or not in the duct 13 or assisting in the determination of water concentration.

The means (M1) is a special integral system comprising a temperature sensor, ultrasound propagation velocity meter, and either an electrical conductivity meter or a viscometer and adapted to be computer-controlled. The computer is loaded with a program by which the three physical quantity data from said respective instruments are converted to the concentration of water (or hydrogen fluoride) according to the memorized calibration data on the relationship of the concentrations of components of a ternary mixture with said three physical quantities.

The means of (M2) and flow control valve 26 can control automatically so that they are associated with each other in a known matter, and the control system is established according to a known matter so that it totally controls the necessary amount of the sulfuric acid with adjustment of the amount of the sulfuric acid through the duct 12 corresponding to the amount of sulfuric anhydride added by means (M2).

In said means (M2), the ultrasonic transmitter of said ultrasound propagation velocity meter, the transmitter of said electrical conductivity meter, and the ultrasonic transmitter of said viscometer are disposed in strategical locations of the production plant and the devices for converting electric signals from those transmitters are disposed in an instrument booth, with the respective transmitters being connected to the corresponding converters with conductors.

Using the above apparatus, 1125 kg/Hr of hydrogen sulfide was continuously produced from 2250 kg/Hr of feed fluorspar and 3022 kg/Hr of feed sulfuric acid. The concentration of water in the high-boiling mixture (b) available from the kiln was about 14.7 weight %. Therefore, 252 kg/Hr of sulfuric anhydride and 648 kg/Hr of sulfuric acid were added as 900 kg/Hr of 28 weight % fuming sulfuric acid. Separately, 1480 kg/Hr of sulfuric acid was further added.

Applying the above water concentration determination method, the plant was operated under substantially the same conditions for 30 days. As a result, the water content of sulfuric acid feed to the kiln was consistently controlled within +2.5 weight % and no trouble was encountered at all.

INDUSTRIAL APPLICABILITY

The method of the invention for determining the concentrations of components of a ternary mixture enables a high-precision, rapid measurement of the water concentration of the 3-component mixture. Furthermore, the process of the invention for continuous production of hydrogen fluoride comprising the use of the method enables production of hydrogen fluoride with utmost safety and high efficiency.

What is claimed is:

1. A process for continuous production of hydrogen fluoride comprising the following steps (1) to (5):

(1) a step of reacting feed fluorspar with feed sulfuric acid, (2) a step of separating a crude product from said step (1) into (a) a low-boiling mixture composed predominantly of hydrogen fluoride and (b) a high-boiling mixture composed predominantly of unreacted sulfuric acid and containing small proportions of hydrogen fluoride and water, (3) a step of purifying and isolating hydrogen fluoride from said low-boiling mixture (a), (4) a step of adding sulfuric anhydride to said high-boiling mixture (b) in an amount substantially equivalent to the amount of water contained therein for reaction to form sulfuric acid to thereby convert substantially all the water to sulfuric acid and returning it together with unreacted sulfuric acid feed to said step (1), wherein the amount of water occurring in a high-boiling mixture (b) is determined by a method for determining the concentration of water of a ternary mixture essentially consisting of sulfuric acid, hydrogen fluoride, and water, which comprises measuring at least one set of three physical quantities (1) temperature, (2) ultrasound propagation velocity, and (3) electrical conductivity or viscosity, of said ternary mixture and converting measured values to the concentration of water with reference to separately pre-constructed calibration curves representing the relationships of concentrations of respective components of a ternary mixture of sulfuric acid, hydrogen fluoride, and water to said three physical quantities, and (5) a step of supplying a supplemental amount of sulfuric acid as to make substantially the total necessary amount of sulfuric acid available for reaction with feed fluorspar.

2. The process according to claim 1 wherein two sets of the three physical quantities are measured and converted to the concentration of water.

3. The process according to claim 2 wherein the method of measuring the three physical quantities of temperature, ultrasound propagation velocity, and electrical conductivity and converting measured values to the concentration of water is used in said step (4) and the method of measuring the three physical quantities of temperature, ultrasound propagation velocity, and viscosity and converting measured values to the concentration of water is used in said step (5).

4. The process according to claim 1 wherein the ranges of concentrations of components of the ternary mixture to be analyzed are 70 to 100 weight % for sulfuric acid, 0 to 30 weight % for hydrogen fluoride, and 0 to 30 weight % for water, the total concentration of which is 100 weight %.

5. The process according to claim 1 wherein the calibration curves are shown in FIG. 1 or FIG. 3.

6. The process according to claim 1 wherein in step (4) the temperature (1) is 15 to 45° C.

7. The process according to claim 1 wherein the ternary mixture for determination of the three physical quantities is a liquid system.

8. The process according to claim 1 wherein the amount of water occurring in the high-boiling mixture (b) in the step (4) is determined before adding sulfuric anhydride to the high-boiling mixture (b) by measuring (1) temperature, (2) ultrasound propagation velocity and (3) electrical conductivity, and after adding sulfuric anhydride to the high-boiling mixture (b) by measuring (1) temperature, (2) ultrasound propagation velocity and (3) viscosity.

* * * * *